United States Patent [19]

Goedert

[11] Patent Number: 5,604,588
[45] Date of Patent: Feb. 18, 1997

[54] IMAGING PLASMA IN NONLINEAR LIMITER CELLS

[75] Inventor: Robert V. Goedert, Ferndale, Mich.

[73] Assignee: United States of America as represented by the Secretary of the Army, Washington, D.C.

[21] Appl. No.: 505,519

[22] Filed: Jul. 20, 1995

[51] Int. Cl.$^6$ .................................................. G01N 21/63
[52] U.S. Cl. ........................................................ 356/318
[58] Field of Search ............................................. 356/318

[56] References Cited

PUBLICATIONS

Docchio et al "Study of the temporal and spatial dynamics of plasmas induced in liquids by nanosecond Nd:YAG laser pulses. 1: Analysis of the plasma starting times", Applied Optics vol. 27, #17, 1 Sep. 1988, pp. 3661–3668.

Primary Examiner—Vincent P. McGraw
Attorney, Agent, or Firm—Peter A. Taucher; David L. Kuhn

[57] ABSTRACT

A method to examine laser induced plasma or bubble formations in nonlinear limiter cells includes splitting a laser pulse into an initiation pulse, a first probe pulse and a second probe pulse. The initiation pulse is focussed at a site in the cell, so that a formation of interest occurs there. The probe pulses are converted to frequencies different from each other and different from the initiation pulse frequency. Then the probe pulses are sent through single mode fibers of different measured lengths, so that the probe pulses are retarded relative to the initiation pulse by different, controlled intervals. The probe pulses exit the fibers in coherent collimated condition and travel along a common path crossing the site. The initiation pulse will have arrived at the site and created the formation before the first probe pulse arrives, and the second probe pulse arrives at the site after the first probe pulse. Shadowgraphs resulting from passage of the probe pulses past the formation are then imaged.

14 Claims, 4 Drawing Sheets

IMAGING PLASMA IN NONLINEAR LIMITER CELLS

GOVERNMENT USE

The invention described here may be made, used and licensed by or for the U.S. Government for governmental purposes without paying me royalty.

BACKGROUND

The battlefield of the future may contain laser weapons used to blind the crew of combat vehicles. These future weapons will probably fire laser pulses a few nanoseconds long and will have very high peak power intensities. When such a laser pulse enters the human eye, it is focussed to a very small spot on the retina and burns the retina. These weapons are expected to be "agile," or able to lase unpredictably at any color of light in the visible spectrum, so that simple colored absorbing glass or reflection filters are not viable for protecting the eye. That is, if we use filters to block red laser light, green lasers could blind us and vise versa. Obviously, protective devices absorbing light throughout the visible spectrum are not a viable option either, since no spectra would then be available for vision. To neutralize future laser threats, a material or device acting independently of wavelength is needed which passes low energy light (such as normal scene illumination) to the eye while blocking high energy light. A device or material operating in this fashion is said to be nonlinear in energy. A vision system using a nonlinear absorbing or scattering material is described in my U.S. Pat. No. 5,345,340 issued Sep. 6, 1994.

One concept for nonlinear laser protection is a suspension cell limiter such as a carbon black suspension cell (CBS). In a CBS, nonlinear blocking is achieved by focussing incident light into a cell containing a suspension of carbon particles. The energy absorbed by any carbon atom is greater than the work function of an electron within the atom so that the electron escapes, thereby causing a free electron and a C+ ion. A collection of these electrons and ions is called a plasma. Plasmas can be very energetic and dense and can be very strong absorbers or reflectors of photons. Once the beginning of an incident laser pulse has initiated a plasma, the plasma absorbs and scatters the rest of the pulse. Additionally, heat from the plasma vaporizes the solvent and the resultant bubbles act to scatter light incident on the CBS.

Another nonlinear laser protection method uses sacrificial mirrors. Sacrificial mirrors are mirrors which damage easily and oblate (blow away) when high energy light strikes them, whereby less of the laser pulse is reflected to the eye. Still another concept involves the use of nonlinear absorbers, which have an electronic structure whose ground state is not highly absorbing to visible wavelengths but whose excited state is very strongly absorbing to visible photons. In nonlinear absorbers, low densities of photons (from background illumination) do not pump enough electrons into highly absorbing exited states to effect appreciable absorption. However, the high photon density of the beginning of a laser pulse drives enough electrons to the exited states to absorb the rest of the pulse.

The phenomena occurring during nonlinear absorption or scattering of laser light are extremely rapid. For example, a laser light pulse is typically 10 nanoseconds long, and it is believed that plasmas are formed within a few nanoseconds of a laser pulse becoming incident on a CBS. In order to study these phenomena, it is very helpful And perhaps necessary to measure various facets of their temporal and spatial dynamics. Such facets include: time needed for plasma initiation, time needed for bubble initiation, energies needed for these initiations, the shape and rate of bubble or plasma growth over time, and length of bubble and plasma life. Pioneering work in measuring spatial and temporal dynamics has been done by Franco Docchio, Pietro Regondi, Malcom R. Capon and John Mellerio and published in their article, "Study of the Temporal and Spatial Dynamics of Plasmas Induced in Liquids by Nanosecond Nd:YAG Laser Pulses. 1: Analysis of Plasma Starting Times," Applied Optics, Vol 27, No. 17, September 1988. Docchio et. al. used a flashlamp and steak camera to obtain a framing rate of $20 \times 10^6$ frames per second.

SUMMARY OF THE INVENTION

My technique images the aforementioned spatial and temporal dynamics at an image capture rate which is an order of magnitude faster than the method used by Docchio et al. This technique is intended to image laser induced plasma formations inside a CBS and measure the plasma's size, growth rate, lifetime, and energy of initiation. This technique is capable of measuring laser induced bubble formations in similar fashion. Plasma and bubble formation in non-CBS cells can be imaged as well, and the technique can be extended to examine mirror oblations, damage to optical glass, non-linear absorption by materials that do not form a plasma, or other extremely fast events that occur during nonlinear absorption or scattering of incident laser light. The technique can also be used to image extremely fast phenomena in powder suspensions or to image extremely fast flows of particles.

In my technique a pulse of laser light is split into a plasma initiation pulse, a first probe pulse and a second probe pulse. The initiation pulse is focussed at a site in a nonlinear limiter cell so that a plasma or bubble formation occurs there. The probe pulses are converted to wavelengths different from each other and different from the initiation pulse wavelength. Then the probe pulses travel through optical fibers of differing measured lengths, thereby differentially retarding the probe pulses relative to the initiation pulse. The probe pulses exit the fibers and travel, one after the other, along a common path through the plasma initiation site, where the initiation pulse will have already arrived and created the formation. Shadowgraphs resulting from passage of the probe pulses past the formation are then imaged and sent to a frame grabber.

DETAILED DESCRIPTION

Figure 4:
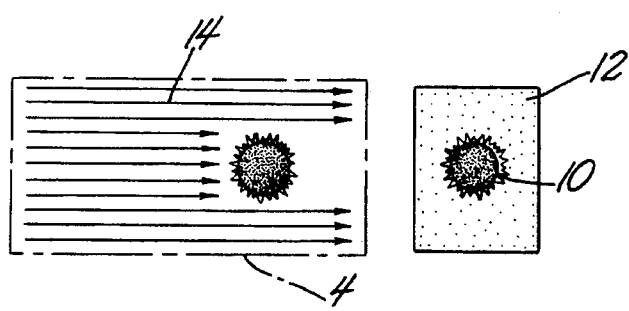
FIG. 4 is an idealized representation of shadowgraph creation.

My technique produces shadowgraphs of a plasma 8 (shown in idealized fashion in FIG. 4) or other disturbance in a volume of material 4 where incoming laser light (not shown in FIG. 4) is focussed. Material 4 can be a carbon black suspension, water, neat methanol, methanol with ink added, neat toluene, toluene with motor oil added or any fluid, including air, that one desires to test. FIG. 4 has a conceptual representation of a shadowgraph 10 of plasma 8 produced on the focal plane 12 of a camera. The shadowgraph forms when collimated imaging light from a probe pulse, represented by rays 14, is projected from behind plasma 8 toward focal plane 12. Since plasma 8 absorbs or scatters light, rays 14 that strike plasma 8 do not reach plane 12, whereby an unlit area is formed on the plane. This area is shadowgraph 10.

Figure 1:
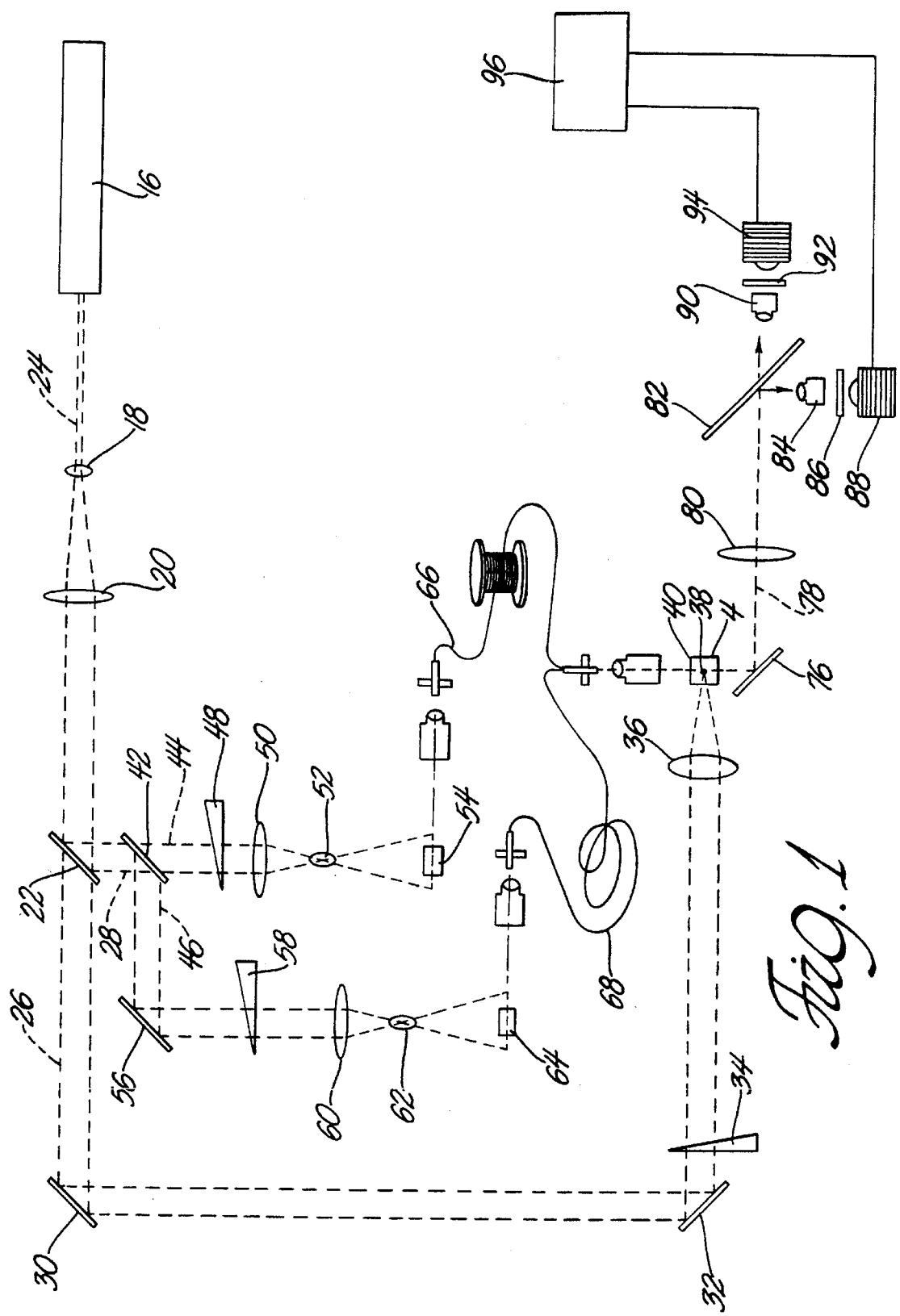
FIG. 1 is a diagram of the apparatus used in my technique to create shadowgraphs of plasma or bubble formations in nonlinear limiter cells.

FIG. 1 is a diagram illustrating how my technique is performed. A Q-switched doubled Nd:YAG laser at 16 provides a highly coherent laser beam 24 in the form of a 532 nm wavelength gaussian pulse with a duration of 9.6 ns at full width, half maximum (FWHM). The 9.6 ns duration was selected because it approximates the duration of agile laser beams likely to be encountered in a battlefield scenario. Beam 24, represented by parallel dashed lines, is expanded in conventional fashion by lenses 18 and 20. The purpose of expanding beam 24 is to lessen its intensity and thereby prevent damage to mirrors and other optical components downstream of the laser. Too, as a practical matter, wide beams can be focussed to a smaller focal area than narrow beams. After beam 24 is expanded, it is split, again in conventional fashion, by partial mirror 22 into a collimated plasma initiation pulse 26 and a pulse component 28 from which collimated probe pulses will be derived. Plasma initiation pulse 26 is directed to variable attenuator 34 by flat mirrors 30 and 32 or other suitable means of directing light. The function of variable attenuator 34 is to control the intensity of plasma initiation pulse 26 and is typically a variable density partially reflecting mirror, a filter, or a band divided into segments having varying light transmittal percentages.

Figure 2:
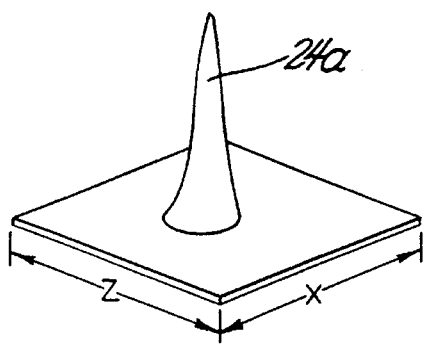
FIG. 2 is the spatial profile of the laser output, this profile exhibiting s gaussian distribution.
Figure 3:
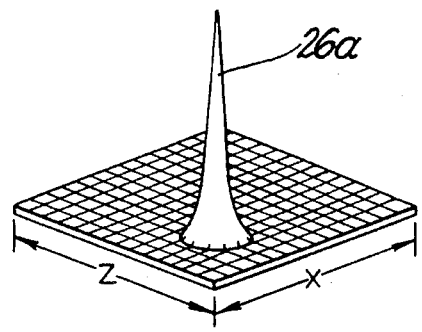
FIG. 3 is the spatial profile of the focal spot at the plasma initiation site, this profile, too, exhibiting a gausian distribution.

Next, plasma initiation pulse 26 is focussed by achromatic lens 36, which typically has a focal length of 80 mm and a focussing value of f/15, although focal length and f/# are variable. Also typically, pulse 26 is focussed from an $1/e^2$ beam diameter of 5.36 to a focal spot whose $1/e^2$ beam diameter is 20 µm and whose FWHM beam diameter is 10 µm. The focal spot is located at site 38 in a suspension cell 40, which can be a CBS, and plasma initiation occurs at site 38. FIGS. 2 and 3 are the spatial profiles of the laser output (beam 24) and the focal spot respectively. In those figures, cross sections of the beam or spot lie in the x-z plane and the three dimensional spike-like formations 24a and 26a show relative light intensity at points in the cross sections. In both FIG. 2 and in FIG. 3, the light intensities have a gaussian distribution.

Figure 6:
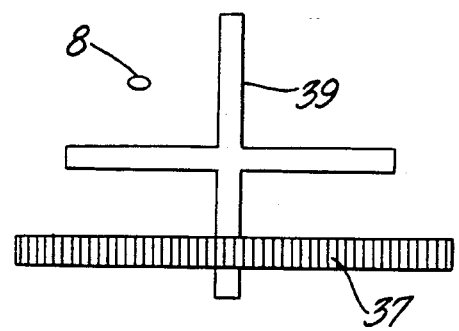
FIG. 6 shows an optional gauging means for the plasma initiation site.
Figure 5:
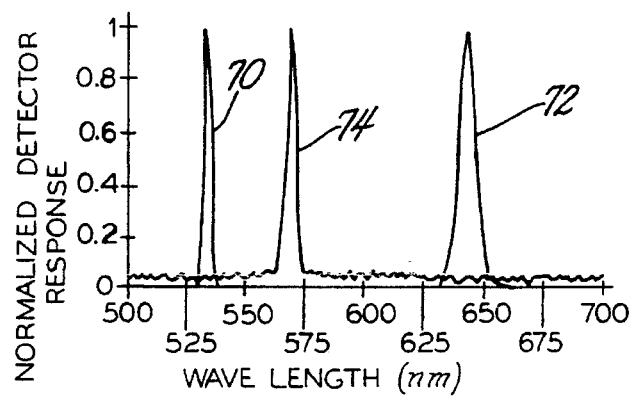
FIG. 5 shows the wavelength ranges for the probe pulses and the plasma initiation pulse.

A suspension cell 40 was used that comprised a cuvette having inner dimensions of 5 mm by 10 mm, but inner cuvette dimensions of 5 mm by 5 mm or 2 mm by 2 mm may be preferred. The plasma initiation pulse 26 was focussed through the 5 mm path length and the collimated probe pulses passed through the 10 mm path of the cell. Optionally, a gauging means such as a length scale 37 (FIG. 6), typically 50 µm per division, is used to calibrate the system to measure the plasma or bubble size. The gauging means may include a cross hair arrangement 39 (FIG. 6) of known orientation within the cell. The cross hair arrangement can be fixed at site 38 and can be used to align the probe pulses perpendicular to the plasma initiation pulse.

Immediately after beam 24 is split into initiation pulse 26 and component pulse 28, component pulse 28 is split by partial mirror 42 into two highly coherent collimated probe pulses 44 and 46, which will later illuminate (back light) plasma 8, bubbles or other phenomena at site 38. In order for the probe pulses to be useful, they must undergo conditioning steps. First, since plasma 8 is thought to live for 500 ns or less, it is necessary that the probe pulses be short so as not to wash out the CCD cameras 88 and 94 (FIG. 1) during the cameras' staring cycle time. That is, if one uses a continuous light source for the probe, then a short (500 ns) blocking of the light source will not be detected. The shorter the probe pulses, the faster will be the effective exposure time for imaging phenomena at site 38. Also, since the plasma initiation pulse is 9.6 ns FWHM, it would be desirable to make at least one probe pulse duration a fraction of the plasma initiation pulse duration, whereby one can distinguish events occurring during the passage of initiation pulse 26 through site 38.

Further conditioning of the probe pulses is needed. Plasma 8, once created, scatters some of the green laser light (532 nm wavelength light from pulse 26), which can effectively fill the shadow created by the plasma's interruption of the probe pulses. Thus the probe pulses must be of different wavelengths from plasma initiation pulse 26 so that the scattered portions of pulse 26 can be eliminated from the imaging systems by use of a filter. Accordingly, once probe pulse 44 is formed, it is passed through variable attenuator 48, is focussed by lens 50, and is then focussed by cylindrical lens 52 to a straight line lying along the axis of DCM dye cell 54. Probe pulse 44 thereby becomes a pulse of red light having a narrow band of wavelengths centered at a wavelength value of 643 nm. In similar fashion, after probe pulse 46 reflects off mirror 56, probe pulse 46 is passed through variable attenuator 58, is focussed by lens 60 and is then focussed by cylindrical lens 62 to a straight line lying along the axis of Rhodamine 590 dye cell 64. Probe pulse 46 thereby becomes a pulse of green light having a narrow band of wavelengths centered at a wavelength value of 568 nm. DCM and Rhodamine 590, used in respective dye cells 54 and 64, are both commercially available laser dyes exhibiting fluorescence, or luminescence persisting for less than about $10^{-8}$ seconds after excitation. Laser dyes such as DCM or Rhodamine 590, when pumped by 532 nm light, will emit a pulse of light at a different wavelength.

The red and green probe pulses are passed through specific lengths of single mode optical fiber to effect controlled delay of the probe pulses' arrival at the plasma site. Mirrors can be used for this purpose but doing so has been found to be cumbersome, especially when delays of hundreds of nanoseconds are required. Additionally, single mode fibers advantageously clean up the spatial characteristics of the probe pulses so that light intensity on cross sections of the probe pulses is more uniformly distributed. A single mode fiber 3.8 µm in diameter can be used to obtain a speckle-free collimated illumination field, whereby good quality shadowgraphs can be produced.

Under the conditions of my tests, probe pulse 46 has an output pulse width of 5.8 ns at FWHM and probe pulse 44 has a 9.4 ns FWHM pulse width. It can thus be seen that the probe pulses are shorter than the pulse width of beam 24 from which they were derived. Probe pulse 44 travels through 16.94 meters of single mode fiber 66 and arrives at site 38 70 ns after plasma initiation pulse 26 arrives. Probe pulse 46 travels through 3.74 meters of single mode fiber 68 and arrives at site 38 12 ns after pulse 26. The normalized spectral distribution of plasma initiation pulse 26, probe pulse 44 and probe pulse 46 are shown respectively at 70, 72, and 74 in FIG. 3, where it can be seen that plasma initiation pulse 26 is centered at 532 nm. As mentioned, probe pulse 44 is centered at 643 nm and probe pulse 46 is centered at 568 nm.

Within suspension cell 40, the first event of interest is the arrival of plasma initiation pulse 26 at plasma initiation site 38. Assuming the fluence of pulse 26 is sufficient, a formation of plasma and/or bubbles occurs at site 38. Then green probe pulse 46 arrives in cell 40 on a path perpendicular to the path of the plasma initiation pulse 26, and plasma or bubbles at site 38 will absorb or scatter a portion of pulse 46, whereby a green-light shadow or shadowgraph of the formation will be projected upon mirror 76. Finally, red probe pulse 44 arrives in cell 40 on the same path as probe pulse 46, and plasma or bubbles at site 38 will absorb or scatter a portion of pulse 44, whereby a red-light shadow or shadowgraph of the formation will be projected upon mirror 76.

First green probe pulse 46 and then red pulse 44 are reflected from mirror 76 along path 78 through achromatic imaging lens 80, which in my tests had a 100 mm focal length. Then the probe pulses sequentially arrive at a dielectric reflection filter 82, where red probe pulse 44 is reflected to 5× objective lens 84 and then through RG-610 absorption filter 86, which subtracts scattered 532 nm light waves from the shadowgraph imaged by a COHU 4800 CCD camera 88. Green probe pulse 46 passes through reflection filter 82, through 5× objective lens 90, and then through OG-550 absorption filter 92, which subtracts scattered 532 nm light waves from the shadowgraph imaged by another COHU 4800 CCD camera 94. The combination of lens 80, one of the 5× objective lenses and one of the cameras effects an image enlargement of 139× on the video screen, and a different image magnification can conveniently be accomplished by changing the objective lenses. The magnified images from cameras 88 and 94 are sent to frame grabber system 96.

The onset of laser initiated plasma or bubbles can be determined under the foregoing technique by incrementally advancing or delaying the green probe pulse's arrival at plasma initiation site 38, and then documenting the presence or absence of plasma. The lifetime of laser initiated plasma or bubbles then can be determined under the foregoing technique by incrementally delaying the red probe pulse's arrival at plasma initiation site 38 but not changing the green probe pulse's arrival time, and then documenting the presence or absence of plasma at the red pulse's arrival. Similarly, the plasma and bubble growth rates can be determined by measuring their change in size over various combinations of delay between probe pulses. The arrival times of probe pulses can be varied by changing the lengths of single mode fibers 66 and 68.

Under the FIG. 1 arrangement, an approximate determination of plasma initiation energy was achieved, but a more precise determination could be achieved by synchronizing the FIG. 1 arrangement to a commonly available picosecond pulse length laser for the probe pulses.

In some cases, determining that a particular body in a shadowgraph is a plasma may require allowing a portion of emitted light from the plasma to enter the shadowgraph. In such a determination, it is expected that one will be able to distinguish the center of the plasma from other phenomena detected in the shadowgraph by using a narrow notch filter which blocks the 532 nm light scattered by the plasma but which allows light from the plasma's emitted spectra to pass. Such a filter could replace either or both filters 86 and 92 in FIG. 1 in order to obtain an image from the plasma's emitted spectra.

Figure 7:
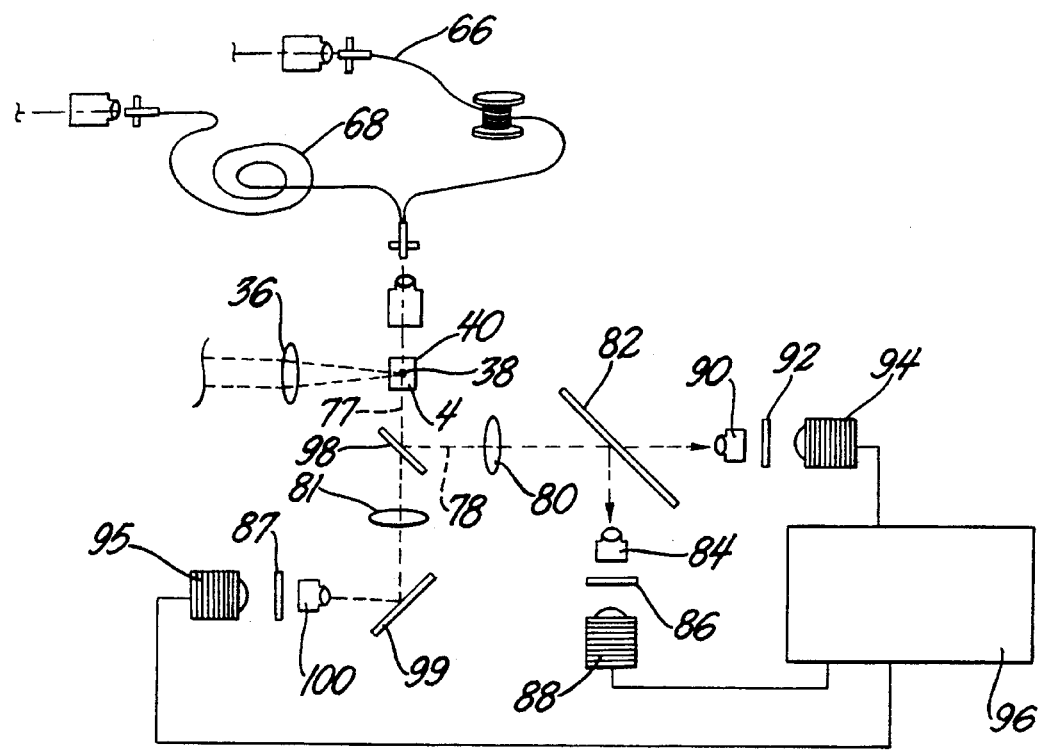
FIGS. 7, 8 and 9 show optional modifications to the apparatus shown in FIG. 1.

Another way of obtaining an image from the plasma's emitted spectra is explained in conjunction with FIG. 7, which shows a partial modification of the FIG. 1 diagram. In FIG. 7, mirror 98 replaces mirror 76, mirror 98 being fully reflective but smaller in size than mirror 76. Mirror 98 lies partly in the path 77 of light exiting cell 40, whereby a first portion of the beam from cell 40 strikes mirror 98, then is fully reflected along path 78 through achromatic lens 80, and then is imaged as discussed above in conjunction with FIG. 1. The second, remaining portion of the beam from cell 40, which is completely unobstructed by mirror 98, passes through achromatic imaging lens 81, strikes fully reflective mirror 99, and passes through 5× objective lens 100. The second portion of the beam then passes through narrow notch filter 87, which blocks the 532 nm light scattered by the plasma but which allows light from the plasma's emitted spectra to pass. Finally the second portion of the beam enters CCD camera 95, which sends an appropriate image to frame grabber 96.

Figure 8:
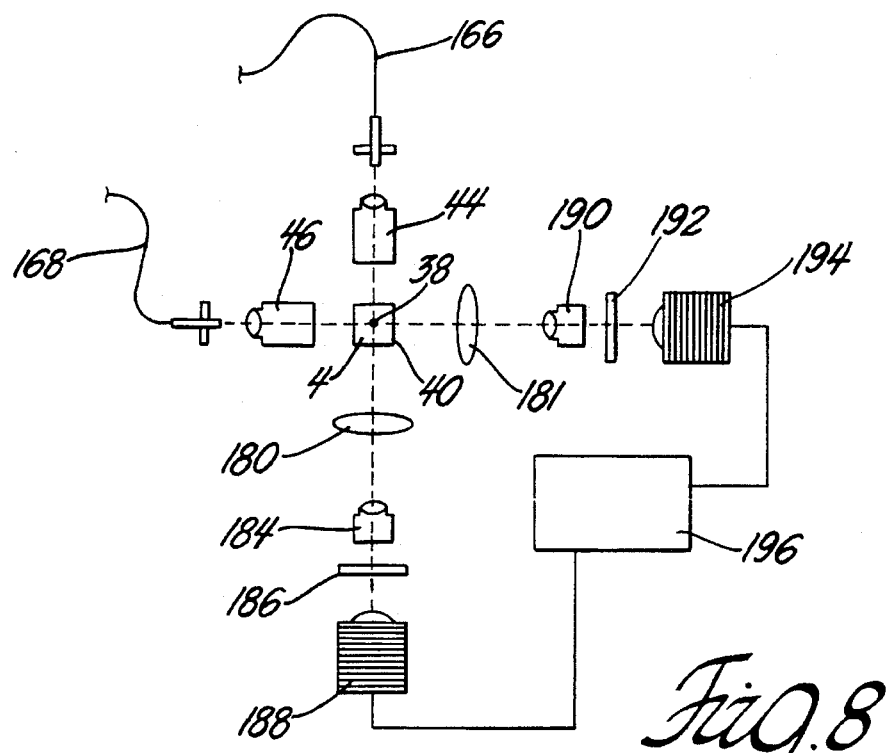

It is contemplated that one may wish to image bubble or plasma formations at site 38 simultaneously from two directions. FIG. 8 shows the elements optically downstream from dye cells 54 and 64 that would be used to accomplish such simultaneous imaging. In that figure, single mode fiber 166 will receive probe pulse 44 from dye cell 54 and single mode fiber 168 will receive probe pulse 46 from dye cell 64. Fibers 166 and 168 are equal in length so that probe pulses 44 and 46 will arrive at site 38 simultaneously but controlledly later than initiation pulse 26. In FIG. 8, the probe pulses arrive at site 38 along paths normal to each other and normal to the path of plasma initiation pulse 26, which travels toward the observer in FIG. 8. However, the probe pulses need not be normal to one another and need not be normal to the plasma initiation pulse. Red probe pulse 44 exits cell 40, passes through achromatic imaging lens 180, through 5× objective lens 184 and then through RG-610 absorption filter 186, which subtracts scattered 532 nm light waves from the shadowgraph imaged by CCD camera 188. Green probe pulse 46 passes through achromatic imaging lens 181, through 5× objective lens 190 and through OG-550 absorption filter 192, which subtracts scattered 532 nm light waves from the shadowgraph imaged by CCD camera 194. The cameras' images are transferred to frame grabber system 196.

Figure 9:
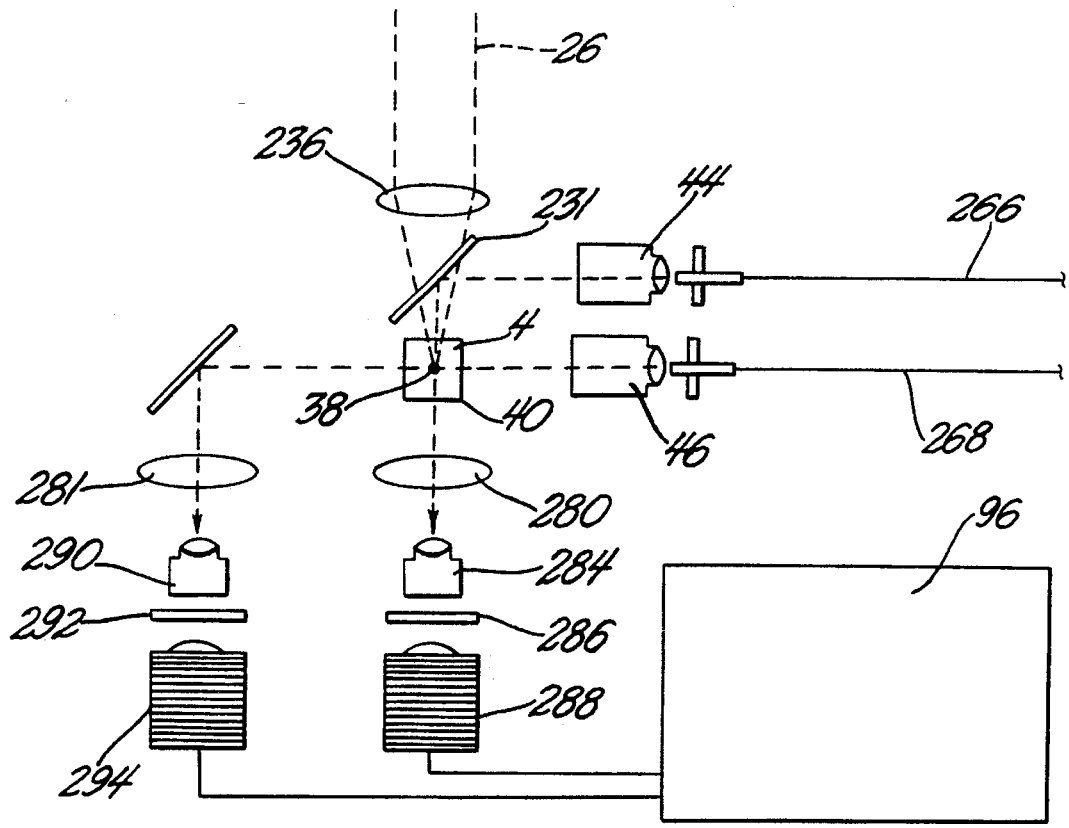

FIG. 9 shows the elements optically downstream from dye cells 54 and 64 used in an alternate technique to image bubble or plasma formations simultaneously from two directions. In that figure, initiation pulse is focussed at site 38 by achromatic lens 236, the converging portion of pulse 26 passing unobstructed through a beam splitter in the form of partially reflective mirror 231. Fiber 266 receives probe pulse 44 from dye cell 54 (not shown in FIG. 9) and fiber 268 receives probe pulse 46 from dye cell 64 (not shown in FIG. 9). Fibers 266 and 268 are equally long, and the probe pulses arrive at site 38 together but a controlled time later than initiation pulse 26. After leaving fiber 266, red probe pulse 44 reflects off mirror 231 and then travels along the path taken by pulse 26, entering cell 40 and passing through site 38. Pulse 44 then exits cell 40, passes through achromatic imaging lens 280, through 5× objective lens 284 and then through RG-610 absorption filter 286, which subtracts scattered 532 nm light waves from the shadowgraph imaged by CCD camera 288. After leaving fiber 268, green probe pulse 46 enters cell 40 and passes through site 38. Pulse 46 then passes through achromatic imaging lens 281, through 5× objective lens 290 and through OG-550 absorption filter 292, which subtracts scattered 532 nm light waves from the shadowgraph imaged by CCD camera 294. The cameras' images are transferred to frame grabber system 296.

I do not desire to be limited to the exact details of construction or method shown herein since obvious modifications will occur to those skilled in the relevant arts without departing from the spirit and scope of the following claims.

What is claimed is:

1. A method to examine a laser induced formation in a material, comprising:

producing a collimated coherent pulse from a laser;

splitting the collimated coherent pulse into an initiation pulse, a first probe pulse and a second probe pulse, wherein the initiation pulse has a given wavelength range, and wherein the probe pulses are of shorter duration than an expected life of the formation;

focussing the initiation pulse at a site in the material, so that a formation initiates at the site;

converting the first probe pulse to a first new wavelength range different from the given wavelength range;

converting the second probe pulse to a second new wavelength range different from the first new wavelength range and different from the given wavelength range;

sending the first probe pulse through a first single mode fiber having a first predetermined length;

sending the second probe pulse through a second single mode fiber having a second predetermined length greater than the first predetermined length;

aligning the first and second probe pulses along a common path in which lies the site, the probe pulses being coherent and collimated;

wherein the initiation pulse arrives at the site before the first probe pulse and the first probe pulse arrives at the site before the second probe pulse;

imaging a first shadowgraph resulting from passage of the first probe pulse past the formation;

imaging a second shadowgraph resulting from passage of the second probe pulse past the formation.

2. The method of claim 1 further comprising the step of causing the first probe pulse to diverge from the second probe pulse after the probe pulses leave the site.

3. The method of claim 1 wherein imaging the shadowgraphs includes a step of removing scattered light of the initiation pulse from at least one of the probe pulses.

4. The method of claim 1 further including:

segregating at least some emitted light of plasma from one of the probe pulses after the one probe pulse exits the material;

using the emitted light so segregated to produce an image of the plasma.

5. The method of claim 1 further comprising fixing a means to gauge formation size and location at the site.

6. A method to examine a laser induced formation, comprising:

producing a collimated coherent pulse from a laser;

splitting the collimated coherent pulse into an initiation pulse and a probe pulse, wherein the initiation pulse has a given wavelength range;

focussing the initiation pulse at a site in a cell so that a formation initiates at the site;

causing a wavelength difference between a probe pulse wavelength range and the given wavelength range;

passing the probe pulse through the site;

delaying the probe pulse's arrival at the site for a chosen time after the initiation pulse arrives at the site;

imaging a shadowgraph resulting from passage of the probe pulse through the site.

7. The method of claim 6 wherein delaying the probe pulse's arrival comprises sending the probe pulse through a selected length of optical fiber.

8. The method of claim 6 wherein the step of causing the wavelength difference between the probe pulse wavelength range and the given wavelength range comprises:

changing the probe pulse wavelength range; and improving the spatial characteristics of the probe pulse.

9. The method of claim 8 including the use of a single means to effect both the delaying of the probe pulse's arrival at the site and the improving of the spatial characteristics of the probe pulse.

10. The method of claim 6 wherein imaging the shadowgraph includes:

after the probe pulse passes through the site, segregating emitted light of plasma from the probe pulse;

after removing the emitted light, using the emitted light to create a depiction of the formation.

11. The method of claim 6 wherein:

during the step of focussing the initiation pulse, the initiation pulse passes through a mirror while converging to the site; and the step of passing the probe pulse through the site includes reflecting the probe pulse off the mirror along a path travelled by the initiation pulse.

12. A method to examine laser induced formations in nonlinear limiter cells, comprising:

producing a collimated coherent pulse from a laser;

splitting the collimated coherent pulse into an initiation pulse, a first probe pulse and a second probe pulse, wherein the initiation pulse has a given wavelength range;

focussing the initiation pulse at a site in the nonlinear limiter cell, so that a formation initiates at the site;

converting the first probe pulse to a first new wavelength range different from the given wavelength range;

converting the second probe pulse to a second new wavelength range different from the given wavelength range;

sending each of the probe pulses to the site through an optical fiber having a predetermined length, whereby the probe pulses arrive at the site controlledly later than the initiation pulse;

aligning the first and second probe pulses along different paths crossing the site, the probe pulses being coherent and collimated;

imaging a first shadowgraph resulting from passage of the first probe pulse past the formation;

imaging a second shadowgraph resulting from passage of the second probe pulse past the formation.

13. The method of claim 11 wherein the probe pulses arrive at the site simultaneously.

14. The method of claim 12 further including:
  segregating at least some emitted light of plasma from one of the probe pulses after the one probe pulse exits the material;
  using the emitted light so segregated to produce an image of the plasma.

* * * * *